United States Patent

Hoffer et al.

[11] Patent Number: 5,824,027
[45] Date of Patent: Oct. 20, 1998

[54] NERVE CUFF HAVING ONE OR MORE ISOLATED CHAMBERS

[75] Inventors: Joaquin Andreas Hoffer, Anmore; Yunquan Chen, Vancouver; Kevin D. Strange, Port Moody; Paul Richard Christensen, Burnaby, all of Canada

[73] Assignee: Simon Fraser University, Burnaby

[21] Appl. No.: 911,604

[22] Filed: Aug. 14, 1997

[51] Int. Cl.[6] .................................................... A61N 1/05
[52] U.S. Cl. .............................. 607/118; 604/93; 600/377
[58] Field of Search .................................. 607/118, 148; 600/372, 373, 377, 393; 604/93, 179, 20, 174, 175, 280, 264

[56] References Cited

U.S. PATENT DOCUMENTS

| | | | |
|---|---|---|---|
| 3,797,485 | 3/1974 | Urquhart | 604/93 |
| 4,341,221 | 7/1982 | Testerman | 600/377 |
| 4,602,624 | 7/1986 | Naples et al. . | |
| 4,934,368 | 6/1990 | Lynch . | |
| 4,940,065 | 7/1990 | Tanagho et al. | 607/118 |
| 5,038,781 | 8/1991 | Lynch . | |
| 5,282,468 | 2/1994 | Klepinski . | |
| 5,303,704 | 4/1994 | Molacek et al. | 600/377 |
| 5,324,322 | 6/1994 | Grill, Jr. et al. . | |
| 5,344,438 | 9/1994 | Testerman et al. . | |
| 5,400,784 | 3/1995 | Durand et al. . | |
| 5,487,756 | 1/1996 | Kallesoe et al. . | |
| 5,496,292 | 3/1996 | Burnham | 604/280 |
| 5,505,201 | 4/1996 | Grill, Jr. et al. . | |
| 5,634,462 | 6/1997 | Tyler et al. . | |
| 5,647,846 | 7/1997 | Berg et al. | 604/93 |

OTHER PUBLICATIONS

Hoffer et al., "Neural signals for Command Control and Feedback in Functional Neuromuscular Stimulation: A Review", Journal of Rehabilitation Research and Development, vol. 33, No. 2, Apr. 1996, 145–157.

Goodall et al., "Position–Selective Activation of Peripheral Nerve Fibers With a Cuff Electrode", IEEE Transactions On Biomedical Engineering, vol. 43, No. 8, Aug. 1996, 851–856.

Primary Examiner—William E. Kamm
Assistant Examiner—Kennedy J. Schaetzle
Attorney, Agent, or Firm—Oyen Wiggs Green & Mutala

[57] ABSTRACT

A nerve cuff has one or more sets of electrodes for selectively recording electrical activity in a nerve or for selectively stimulating regions of the nerve. Each set of electrodes is located in a longitudinally extending chamber between a pair of longitudinal ridges which project into the bore of the nerve cuff. The ridges are electrically insulating and serve to improve the selectivity of the nerve cuff. The ridges seal against an outer surface of the nerve without penetrating the nerve. Nerve cuffs according to the invention may be used in functional electrical stimulation systems. Electrodes may be replaced with fine tubes to enable pharmacological agents to be delivered selectively through the tubes to portions of a nerve passing through the cuff or to permit the sampling of fluids from regions adjacent selected outer portions of the nerve. The nerve cuff may be constructed of modular segments which can be selected to provide a customized fit to the shape and size of a nerve at time of implantation.

28 Claims, 8 Drawing Sheets

NERVE CUFF HAVING ONE OR MORE ISOLATED CHAMBERS

TECHNICAL FIELD

This invention relates to biomedical apparatus and, in particular to implantable nerve cuffs for stimulating nerves and/or recording electrical activity in nerves. The invention is particularly applicable to nerve cuffs equipped with electrodes for stimulating and/or monitoring electrical activity in nerve tissues in human beings or other creatures possessing nervous systems. Nerve cuffs according to the invention may have particular application in functional electrical stimulation ("FES") of the neuromuscular system. This invention may also be used in implantable biomedical devices for introducing, monitoring or removing fluids or other matter from the vicinity of nervous tissues.

BACKGROUND

Nerve cuffs equipped with electrodes may be used for interfacing with the nervous system by recording from or stimulating neural tissues. For example, implanted nerve cuffs have been used to record nerve signals from peripheral nerves in animals in a wide range of experimental conditions. A nerve cuff comprises a tube of a suitable biocompatible material having a bore and a longitudinally extending closure. The bore of the nerve cuff has a diameter which is generally slightly larger than the diameter of the nerve which the cuff will be applied to.

A nerve cuff is surgically implanted around a nerve. Very generally, this is done by dissecting a portion of the nerve away from other tissues, opening the closure of the nerve cuff, placing the nerve cuff around the dissected portion of the nerve and then sealing the closure so that the nerve passes through the bore of the nerve cuff. Electrodes inside the bore may be used to stimulate the nerve, monitor electrical activity in the nerve and/or measure impedance or other electrical characteristics of the nerve. Small tubes may be used to carry fluids, such as medicines into the nerve cuff or to remove fluid samples from within the nerve cuff. Kallesøe et al., U.S. Pat. No. 5,487,756 entitled IMPLANTABLE CUFF HAVING IMPROVED CLOSURE describes a nerve cuff of a type which may be used for stimulating or monitoring electrical activity in nerves.

Nerve cuff electrodes have been used in stimulation systems with the goal of providing partial voluntary control of muscles that have been paralysed as a result of lesions caused by spinal cord injury, stroke, or other central neurological system disorders. In some cases, partial motor function can be restored by stimulating motor neurons or muscles below the level of the lesion. Nerve cuffs may also be used as sources for feedback for the control of closed-loop functional electrical stimulation (FES) systems, for example, the system described in Hoffer, U.S. Pat. No. 4,750,499 entitled CLOSED-LOOP IMPLANTED SENSOR, FUNCTIONAL ELECTRICAL STIMULATION SYSTEM FOR PARTIAL RESTORATION OF MOTOR FUNCTIONS. Hoffer et al., Neural signals for command control and feedback in functional neuromuscular stimulation: a review J. Rehab. Res & Dev. 33:145–157, 1996 reviews the recent developments in the field of FES.

Recently, nerve recording cuff electrodes have been implanted around small nerves in either the hands or legs of neurologically impaired, paralysed human beings. These implanted electrodes were used to obtain sensory nerve signals suitable for controlling FES systems designed to restore some basic hand or leg motor functions. These nerve cuffs included a single circumferential electrode or a single set of circumferential electrodes. These nerve cuffs were incapable of selecting electrical signals arising from particular nerve fibers in the nerve but instead recorded a signal reflecting the aggregate electrical activity generated by all nerve fibers in the nerve.

Useful sensory signals can be obtained using such single channel electrodes. However, single channel electrodes have significant disadvantages in some applications. For example, if it is desired to record sensory signals originating from the nerves in one particular digit with a single channel nerve cuff, it is necessary to place the nerve cuff around a branch of the nerve which originates in that digit before that branch joins nerve branches which originate in other digits. Consequently, such single channel nerve cuffs typically must be surgically implanted around very small nerve branches in the fingers or hand. This requires exacting, time consuming, surgical procedures. Furthermore, once implanted, the small nerves and small nerve cuffs tend to be fragile and, therefore, have a shorter life expectancy than would be the case for a larger nerve cuff applied to a larger nerve. Finally, nerve branches which originate at individual digits tend to extend through relatively exposed places such as the palm of the hand or wrist of a human being. This makes nerve cuffs applied to such nerves even more susceptible to failure.

There has recently been increased interest in the use of nerve cuffs having multiple sets of electrodes. Such multi-contact nerve cuff electrodes may be applied above the point where branches of a nerve combine into a main peripheral nerve trunk. At this point, the nerve and the nerve cuff can be larger, and therefore, more rugged. Furthermore, surgical implantation of a single larger nerve cuff is easier and safer than implanting multiple small nerve cuffs around individual smaller branches of the nerve.

When viewed in cross section, a typical nerve trunk comprises several "fascicles" which are bundles of groups of nerve fibers. Each fascicle contains a large number of nerve fibers or "axons". Each fascicle is encircled by a protective sheath or "perineurium". The fascicles are embedded in a relatively loose matrix of connective tissue or "epineurium" which also contains a vascular supply to the nerve. Blood vessels supplying the various fascicles are highly interconnected in some anatomical locations. Nerve axons frequently cross from one fascicle to another fascicle along the course of a peripheral nerve.

The outer layers of epineurium are generally condensed into a sheath (the "outer epineurial sheath") which encircles the nerve trunk including all of its fascicles and internal blood supply. The outer epineurial sheath delimits the nerve from surrounding structures. A nerve trunk is typically only loosely attached to adjacent anatomical structures by a conjunctival layer.

The outer epineurial sheath can be of variable thickness and toughness. In some anatomical regions along the course of a nerve, for example where fascicles are about to split off from a nerve trunk to form separate nerve branches, the outer epineurial sheath is very thin, the fascicles are not highly interconnected and the fascicles are only loosely connected together by epineurium. In other anatomical regions the outer epineurial sheath may be quite thick and tough and the fascicles may be profusely interconnected by multiple internal exchanges of axons and blood vessels.

Individual fascicles may originate, for example, from individual digits in a person's hand. Ideally, each individual set of electrodes in the multi-contact nerve cuff should stimulate, or record activity from a single fascicle within a nerve trunk, or a specific nerve within a nerve bundle. Because of the exchanges of axons between fascicles, this ideal can not be achieved. There is a need for cuff electrodes which can be used to approach this ideal. Various designs have been proposed for multi-contact nerve cuffs. All of these prior art designs have significant limitations in the context of this intended use.

Some multi-contact nerve cuffs, for example, the nerve cuff disclosed in Naples et al., U.S. Pat. No. 4,602,604 have multiple sets of electrodes on the inner surface of a generally cylindrical electrically insulating nerve cuff having a generally smooth generally cylindrical inside surface. The Naples et al. nerve cuff provides small windows cut through the inner surface of the cuff to expose electrodes which are built into the cuff wall. Similar nerve cuffs are shown in Grill et al. U.S. Pat. No. 5,505,201; Struijk et al., Fascicle Selective Recording With a Nerve Cuff Electrode, Proc. IEEE EMBS, Amsterdam, Netherlands, October, 1996; Sahin et al. Selective Recording With a Multi-Contact Nerve Cuff Electrode, Proc. of 19th Annual International Conference of IEEE EMBS, Amsterdam, Netherlands, October, 1996 and Goodall, Position-Selective Activation of Peripheral Nerve Fibres with a Cuff Electrode, IEEE Trans. On Biomedical Engineering, Volume 43, No. 8, August, 1996, p. 851. These basic designs for multi-contact nerve cuffs have been used both for stimulation of individual subpopulations of axons in a nerve trunk and for recording signals that are generated by different sensor nerve fibre subpopulations eg. axons located in different regions of a nerve trunk, that is enclosed within a multi-contact nerve cuff.

An important problem which has been experienced with such multi-contact nerve cuffs is lack of "selectivity", the ability to identify signals from a particular one of many signal sources or the ability to stimulate preferentially axons in one portion of a nerve. For example, if it is desired to obtain a feed-back signal originating from a single digit with a multi-contact nerve cuff which is implanted around a portion of nerve which includes branches extending to several digits, then it is difficult to arrange the multi-contact nerve cuff so that one set of electrodes produces an output signal which provides feedback only from the selected digit and not from any other digit or digits.

One prior art method for achieving greater selectivity is to sew fine wire electrodes into or around individual fascicles in a nerve trunk. As the fine wire electrodes are each associated most closely with a single fascicle in a nerve trunk or with a single nerve in a nerve bundle, the fine wire electrodes can be very selective. However, implanting such fine wire electrodes requires painstaking surgery and, once implanted, the fine wire electrodes can fail prematurely for various reasons.

Durand et al., U.S. Pat. No. 5,400,784 discloses another multi-channel nerve cuff. The Durand et al. nerve cuff has electrodes located on fin members. The fin members are attached to spring members which are self-biased to slowly urge the fin members to penetrate a nerve trunk at a predetermined rate. It is claimed that the blunt fins in the Durand et al. nerve cuff slowly displace fascicles in a nerve trunk rather than damaging them by piercing the perineurium which encloses each fascicle. There is a concern, however, that the Durand et al. nerve cuff may compress neural tissues and thereby cause nerve damage as its electrodes are urged into a nerve. Furthermore, while the Durand et al. nerve cuff may be readily used in some anatomical locations (e.g. near points where a nerve naturally splits into several branches and is therefore no longer wrapped in tough outer epineurial sheath) the Durand et al. nerve cuff is not well adapted for use in other locations where the outer epineurial sheath is tough or where individual fascicles in a nerve are profusely interconnected.

Tyler et al. U.S. Pat. No. 5,634,462 disclose a nerve cuff designed to be placed around a nerve in a stretched configuration. The nerve cuff has corrugations designed to slowly penetrate a nerve and to carry electrodes into the nerve. The Tyler et al. cuff is still not well adapted for use in anatomical locations where the outer epineurial sheath is tough or where interconnections between fascicles would be damaged by the penetrating corrugations. Furthermore, the Tyler et al. cuff is not designed to provide an effective seal around a nerve.

What is needed is a nerve cuff that can be used effectively to selectively stimulate or record from targeted subpopulations of nerve fibers in a nerve and can be used on nerves which could be damaged by penetration.

SUMMARY OF THE INVENTION

This invention provides a multi-electrode nerve cuff which provides good electrical isolation between individual electrodes or sets of electrodes without actually penetrating a nerve. The nerve cuff comprises an electrically insulating tubular cuff body penetrated by a bore for receiving a nerve. A plurality of electrically insulating ridges extend generally longitudinally on an inner surface of the cuff body. The ridges project into the bore. Adjacent pairs of the ridges define a plurality of parallel chambers extending generally longitudinally in the bore. The ridges electrically insulate adjacent chambers from each other. An electrode or a set of electrodes is located in each of a plurality of the chambers. The electrical isolation provided by the ridges allows electrodes in different ones of the chambers to be used to record electrical activity or to stimulate electrical activity selectively in different regions of a nerve.

One embodiment of the invention provides a cuff in which the cuff body comprises a plurality of linked segments. Each of the segments comprising a cuff body portion bearing a longitudinally extending blunt ridge member. Each segment spans a portion of a circumference of the nerve cuff.

A second aspect of the invention provides a nerve cuff comprising a fluid impermeable tubular cuff body penetrated by a bore for receiving a nerve. The cuff body has a closure for permitting passage of a nerve into the bore. A plurality of fluid impermeable rounded ridges extend generally longitudinally on an inner surface of the cuff body and project into the bore. Adjacent pairs of the ridges define a plurality of chambers extending generally longitudinally in the bore. One or more tubes extend into each of a plurality of the chambers for introducing fluid into or withdrawing fluid from the respective chambers. The ridges reduce the contact between fluids in one of the chambers and portions of a nerve's surface adjacent other ones of the chambers. Thus, the chambers permit increased selectivity in both introducing fluids to specific portions of a nerve or sampling fluids from adjacent specific portions of a nerve.

A further aspect of the invention provides a method for establishing a multi-channel interface with a nerve. The method uses a nerve cuff comprising: a tubular cuff body penetrated by a bore for receiving a nerve, the cuff body having a closure for permitting passage of a nerve into the bore; and, a plurality of longitudinal ridges extending generally longitudinally on an inner surface of the cuff body and projecting into the bore, adjacent pairs of the longitudinal ridges defining a plurality of chambers extending generally longitudinally in the bore. The method involves the steps of dissecting a nerve from surrounding tissues; opening the closure and placing the cuff around the nerve with the chambers extending along portions of the nerve; closing the closure, thereby bringing the ridges into sealing contact with an outer surface of the nerve without penetrating the outer surface of the nerve; and, either stimulating selected portions of the nerve by introducing electrical signals or pharmacological agents into selected ones of the chambers or monitoring selected portions of the nerve by measuring electrical potentials in the chambers or sampling fluids from the chambers.

BRIEF DESCRIPTION OF THE DRAWINGS

Drawings which illustrate preferred embodiments of the invention but which should not be construed so as to limit the scope of the invention are appended in which.

DETAILED DESCRIPTION

Figure 1A:
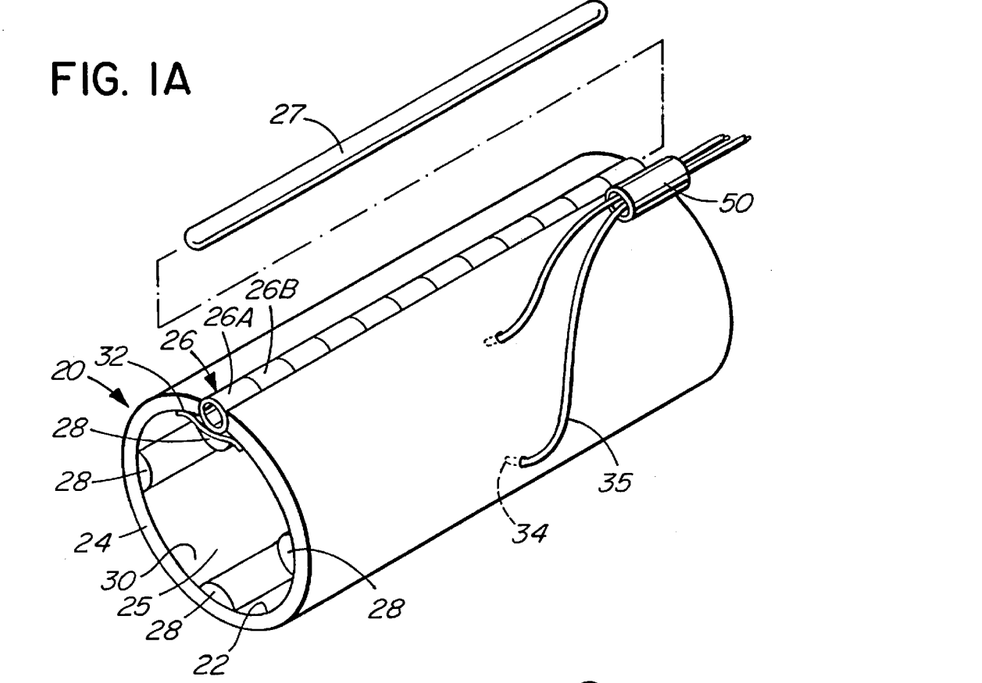
FIG. 1A is a perspective view of multi-channel nerve cuff according to a basic embodiment of the invention.

As shown in FIG. 1A a nerve cuff 20 according to the invention has a tubular cuff body 24 which has an inner surface 22 enclosing a generally cylindrical bore 25 for receiving a nerve. A closure 26 permits cuff body 24 to be opened, placed around a nerve, and sealed with the nerve passing through bore 25.

Closure 26 is preferably a closure of the type described in Kallesøe et al., U.S. Pat. No. 5,487,756, which is incorporated herein by reference. In general that closure comprises a number of spaced apart first apertured members 26A affixed to cuff body 24 at a first edge of a slit in the cuff body and a set of one or more second apertured members 26B capable of being interdigitated between first apertured members 26A and affixed to cuff body 24 at a second edge of the slit. A thin flexible flap 32 is preferably provided to aid in sealing closure 26.

First apertured members 26A and second apertured members 26B have apertures aligned generally with the slit. An elongated locking member 27 can be inserted to extend through the apertures of first apertured members 26A and second apertured members 26B when second apertured members 26B are interdigitated with first apertured members 26A. Locking member 27 may comprise, for example, suture material or a semi-rigid rod.

A plurality of sealing ridges 28 (in the example of FIG. 1A, four ridges 28 at 90 degree intervals around the circumference of bore 25) project inwardly into bore 25. Ridges 28 extend substantially the entire length of cuff body 24. An open sided cavity or "chamber" 30, which extends longitudinally along bore 25, is defined between each pair of adjacent ridges 28. As described below, when nerve cuff 20 is implanted around a nerve, then the nerve closes the radially inwardly facing open sides of chambers 30. Ridges 28 provide electrical and/or fluid isolation between adjacent chambers 30.

Nerve cuff 20 comprises an electrode 34 in each of a plurality of chambers 30. Electrodes 34 may be used, for example, to selectively electrically stimulate fascicles within a nerve (not shown in FIG. 1A) passing through bore 25.

FIGS. 1B, 2, 3 and 4 show a nerve cuff 20A according to an alternative embodiment of the invention in which thin flexible circumferential end sealing ridges 33 extend around bore 25 at each end of ridges 28. Circumferential sealing ridges 33 help to enhance the electrical and/or fluid isolation between different ones of chambers 30 when nerve cuff 20A is implanted around a nerve. Nerve cuff 20A has four groups of electrodes 34 which can each be used, for example, to record electrical activity in a nerve N (FIG. 4) passing through bore 25.

Cuff body 24 comprises a biocompatible material, such as a biocompatible silicone. Where a nerve cuff is to be used for electrical measurements or stimulation the material of the cuff body 24, including ridges 28 and 33, should be electrically insulating. Ridges 28 and 33 may also be formed from silicone. Ridges 28 and 33 should be blunt, are preferably rounded, and most preferably have generally semi-circular cross-sectional profiles, as shown best in FIGS. 2 and 3.

Ridges 28 and 33 preferably comprise a soft fluid impermeable material, such as a soft silicone which will gently seal against the outer epineurial sheath of a nerve trunk without penetrating or excessively indenting the outer epineurial sheath. Ridges 28 and 33 may be formed integrally with cuff body 24 or may comprise separate elements affixed to cuff body 24.

Figures 4, 5A, 5B:
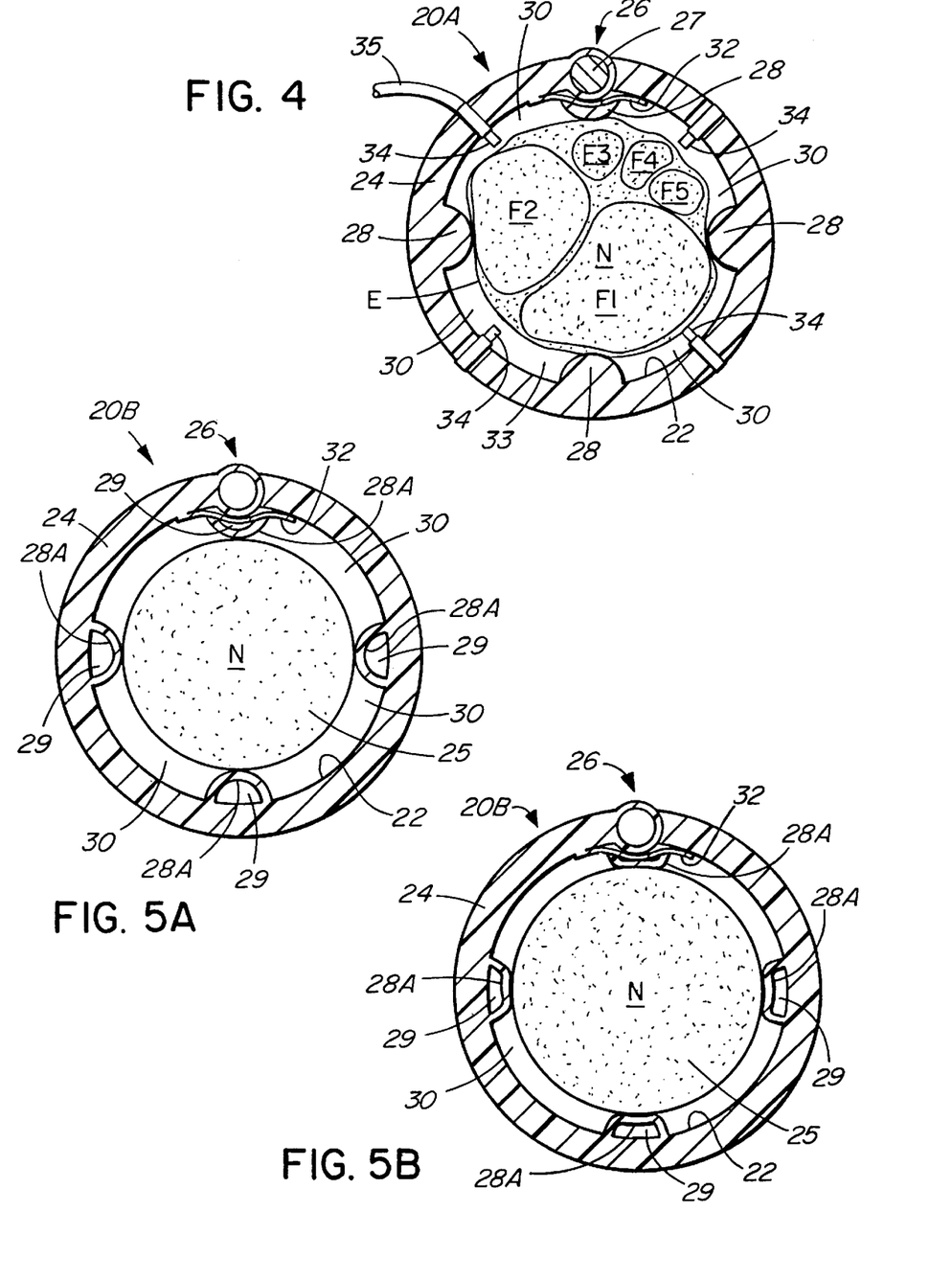
FIG. 4 is a transverse sectional view of the nerve cuff of FIG. 1B implanted around the sciatic nerve of a cat.
FIG. 5A is a sectional view of an alternative embodiment of the invention having tubular sealing ridges in place around a nerve.
FIG. 5B is a sectional view of the embodiment of FIG. 5A with the nerve in a slightly expanded condition.

FIG. 4 shows a cuff 20A in place around a nerve N. Nerve N has a number of fascicles F1, F2, F3, F4 and F5 and is surrounded by a outer epineurial sheath E. It can be seen that each chamber 30 is closed on all sides. Ridges 28 and 33 press against the outer epineurial sheath E of nerve N sufficiently to provide a fluid seal against nerve N. Ridges 28 do not penetrate the epineurial sheath E of nerve N. Each chamber 30 is closed by a pair of ridges 28 on either side, a portion of the inner wall 22 of cuff body 24 on the outside, and a portion of the surface of nerve N on the inside. In the embodiment of FIGS. 1B, 2, 3 and 4, portions of circumferential sealing ridges 33 help to better seal chambers 30 on each end.

FIGS. 5A and 5B show a nerve cuff 20B according to an alternative embodiment of the invention having tubular ridges 28A. Ridges 28A are formed from soft pliable silicone material. The walls of ridges 28A preferably have a thickness in the range of 0.05 mm to 0.25 mm and a hardness of about durometer 30 or less. Ridges 28A are in the form of hollow hemi cylinders having an outside radius of curvature of about 0.2 mm to about 0.5 mm. Each ridge 28A has a longitudinal channel 29. Channels 29 are preferably open at their ends so that body fluids can flow into or out of channels 29 with local changes in fluid pressure.

Ridges 28A may be formed, for example, from lengths of medical grade silicone tubing. The tubing may have an external diameter in the range of about 0.5 mm to 1 mm. Lengths of the tubing can be longitudinally split in half and then affixed in bore 25 with a suitable silicone adhesive. Ridges 28A could also be formed integrally with cuff body 24.

As shown in FIG. 5B, ridges 28A can seal against nerve N and yet can deform to accommodate slight expansions in nerve N without penetrating or significantly indenting nerve N. Tubular ridges 28A may be used with any of the embodiments of nerve cuff described herein.

Figure 5C:
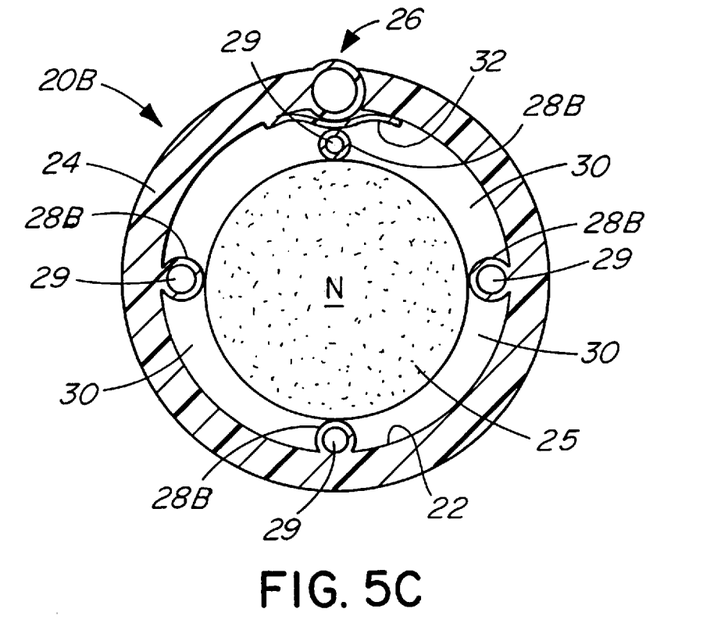
FIGS. 5C is a sectional view of an alternative embodiment of the invention having tubular sealing ridges in place around a nerve.
Figure 5D:
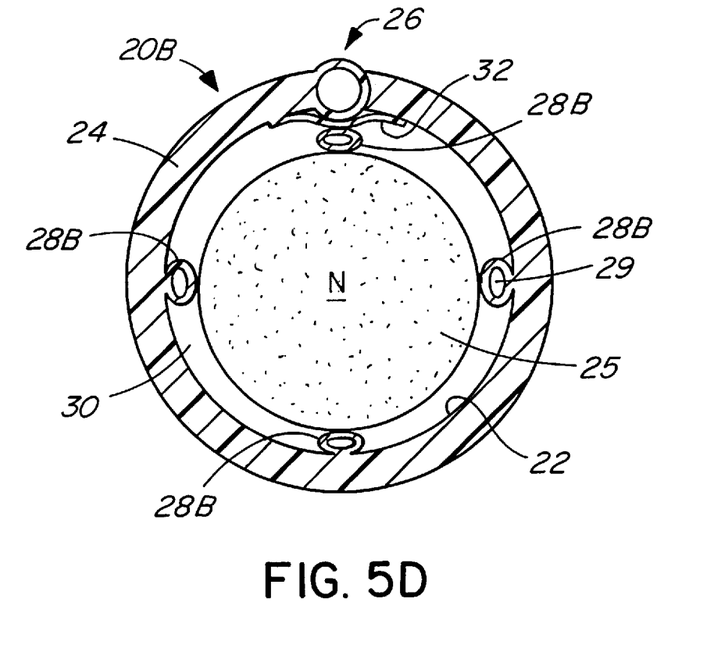
FIG. 5D is a sectional view of the embodiment of FIG. 5C with the nerve in a slightly expanded condition.

FIGS. 5C and 5D show a nerve cuff 20C having hollow cylindrical longitudinal ridges 28B according to another embodiment of the invention. Ridges 28B may comprise, for example, lengths of 0.5 mm external diameter medical grade silicone tubing adhesively affixed to the internal walls of cuff 20C. The tubing should have thin walls which allows it to conform well to the surface profile of a nerve N. Nerve cuff 20C functions in substantially the same manner as nerve cuff 20B of FIGS. 5A and 5B.

Nerve cuffs according to the invention may be used to selectively record electrical signals or other electrical characteristics from portions of a nerve N, to selectively electrically stimulate certain portions of a nerve N, to selectively expose portions of a nerve N to chemical or pharmacological agents or to selectively monitor the compositions of fluids surrounding certain portions of a nerve N.

Cuffs 20 and 20A of FIGS. 1A and 1B through 4 are equipped with electrodes 34 for selectively electrically stimulating a nerve N or for selectively recording electrical activity in portions of nerve N. Those skilled in the art will understand that various configurations and numbers of electrodes 34 may be placed in chambers 30 in cuffs according to the invention. In multi-channel nerve cuffs according to the invention, electrodes 34 (or sets of electrodes 34) are located in two or more of chambers 30.

Figure 1B:
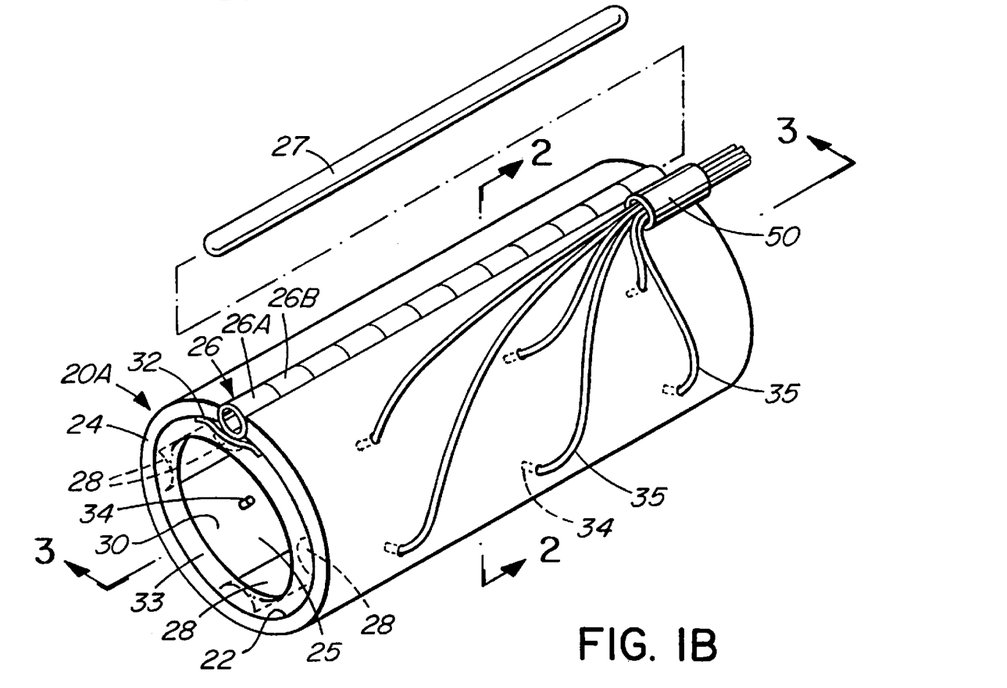
FIG. 1B is a perspective view of a nerve cuff according to an alternative embodiment of the invention having circumferential sealing ridges and four sets of tripolar electrodes.
Figure 2:
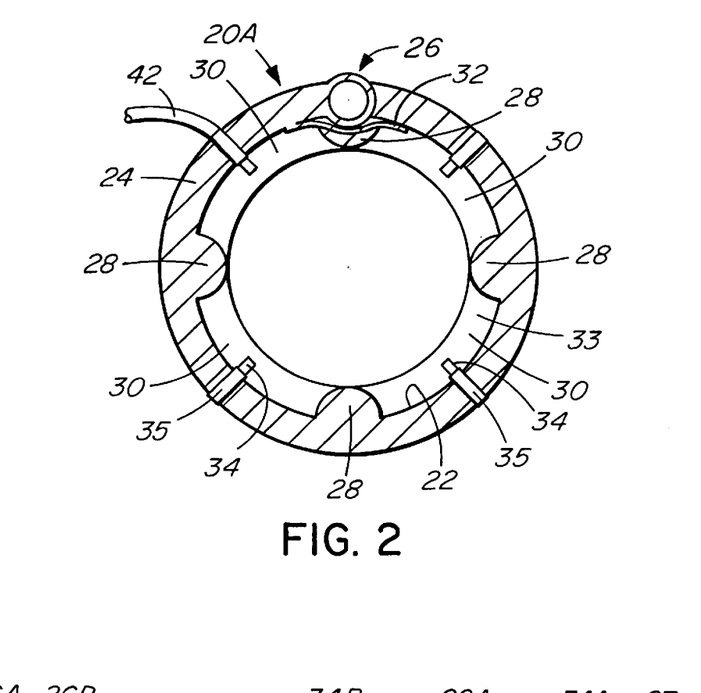
FIG. 2 is a transverse sectional view of the cuff of FIG. 1B along the lines 2—2.
Figure 3:
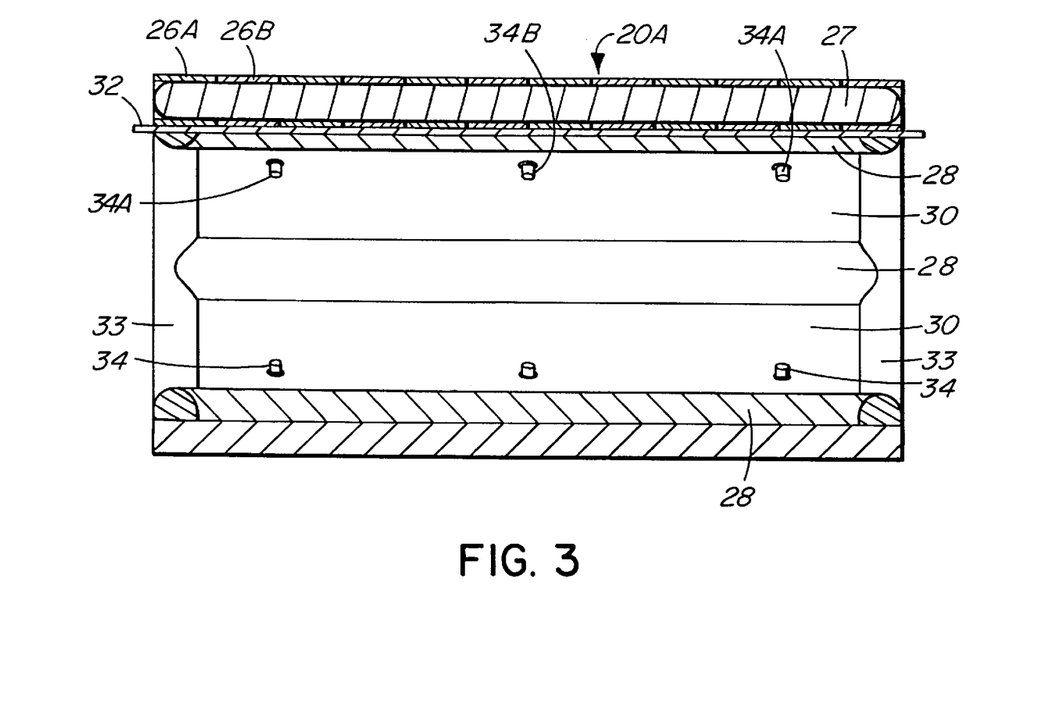
FIG. 3 is a longitudinal sectional view of the cuff of FIG. 1B along the lines 3—3.

Electrodes 34 are in electrical contact with fluids in chambers 30. It is not necessary for electrodes 34 to contact a nerve N passing through bore 25. Electrodes 34 are electrically connected to external equipment (not shown) by insulated wires 35. Wires 35 may be may be embedded in cuff body 24 or routed on the outside or inside of cuff 20. If wires 35 are external to a nerve cuff then wires 35 may pass through a sleeve 50 attached to the nerve cuff (as shown in FIGS. 1A and 1B). In the alternative, electrodes 34 may be connected to miniature amplifiers located in or near the cuff and signals may be transmitted to or from external equipment using radiotelemetry or other wireless means.

In the embodiment of FIG. 1A, each chamber 30 has a single electrode 34. In cuff 20A of FIGS. 1B through 4, a set of three electrodes 34 are located in a balanced tripolar configuration in each chamber 30. Cuff 20A is well adapted for nerve recording applications. Electrodes 34 are equally spaced and centered between ridges 28 in chambers 30. In typical nerve recording applications nerve cuff 20A could be about 10 mm to 50 mm long and electrodes 34 could be spaced apart by up to about one half of the length of cuff 20A.

Electrodes 34 may be connected so that those electrodes 34A (FIG. 3) nearest the opposing ends of each chamber 30 are shorted together. The center electrode 34B can be connected to measuring equipment for measuring nerve action potentials relative to an electrical potential of the two outermost electrodes 34A. Of course, other configurations of electrodes 34 could be placed in chambers 30. Each chamber 30 may have more or fewer than three electrodes 34.

A nerve cuff adapted for nerve stimulation applications could comprise, for example, two electrodes 34 in each chamber 30 separated longitudinally inside the chamber. A large variety of numbers and arrangements of electrodes 34 could be used for nerve stimulation.

The dimensions of a nerve cuff according to the invention will vary depending upon the size of the nerve to which the nerve cuff will be applied. The cuff should be dimensioned so that ridges 28 gently but sealingly contact the outer epineurial sheath of the nerve. For example, a typical nerve cuff for implantation about the sciatic nerve of a cat has a length of about 25 mm and a bore 25 of about 3.5 mm in diameter. A typical nerve cuff for implantation about the median or ulnar nerve of a cat forelimb has a length of about 15 mm and a bore 25 of about 2.5 mm in diameter. Ridges 28 typically project about 0.25 mm to 0.5 mm into bore 25. Ridges 28 typically project into bore 25 by approximately 5% to approximately 20% of an internal diameter of bore 25.

Instead of, or in addition to, making electrical contact with a nerve, a nerve cuff according to the invention could be used to selectively expose portions of a nerve to pharmacological agents or other chemicals or to selectively sample fluids adjacent to portions of the surface of a nerve. In such applications, electrodes 34 are replaced with, or augmented by, one or more tubes 42 connected to deliver or remove small amounts of fluid to chambers 30.

Figure 6A:
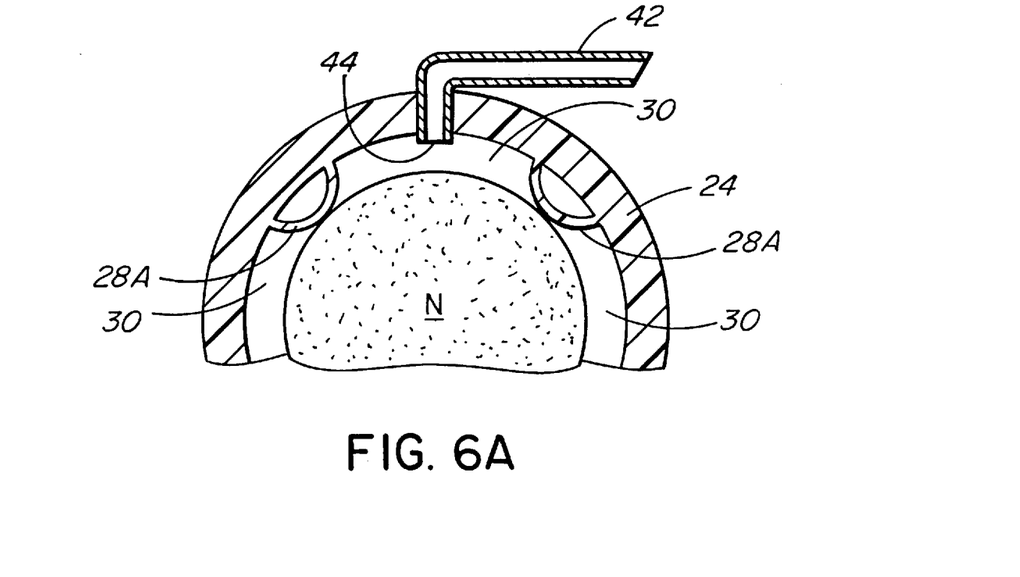
FIGS. 6A and 6B are respectively transverse and longitudinal fragmentary sectional views of a nerve cuff according to the invention having fluid carrying tubes extending into a chamber adjacent a nerve.
Figure 6B:
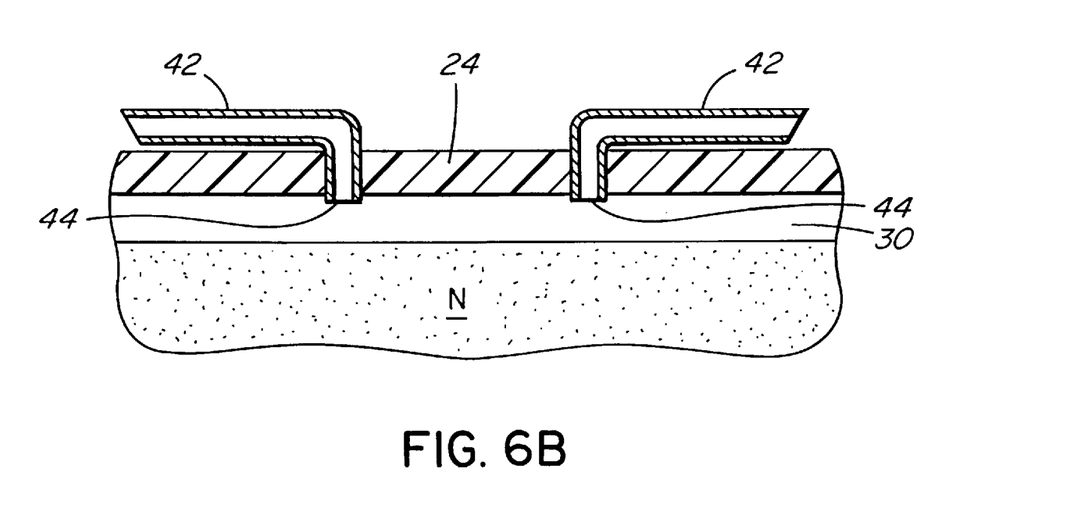

FIGS. 6A and 6B show transverse and longitudinal fragmentary sectional views of a nerve cuff having tubes 42 connected to deliver fluid into (or remove fluid from) a chamber 30 through openings 44. Ridges 28 prevent fluids from one chamber 30 from moving into an adjacent chamber 30. Most preferably two tubes 42 extend into a chamber 30 at longitudinally spaced apart locations. A small amount of fluid can be introduced into chamber 30 via one of the tubes 42 while an equivalent amount of fluid is removed through the other tube 42. Providing two tubes 42 near opposing ends of chamber 30 permits pharmacological agents or other chemicals to be flushed from chamber 30.

Figure 7A:
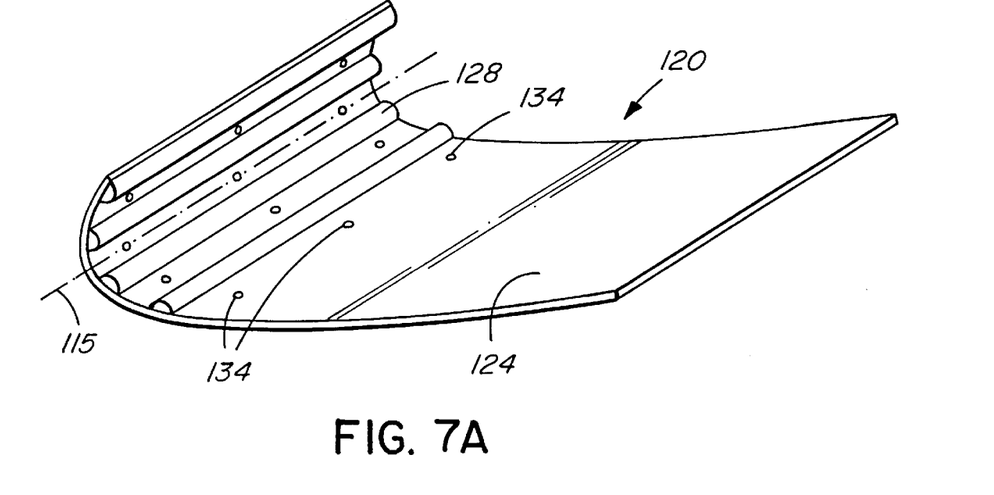
FIGS. 7A and 7B are perspective views of a nerve cuff according to an alternative embodiment of the invention in unrolled and rolled configurations respectively.
Figure 7B:
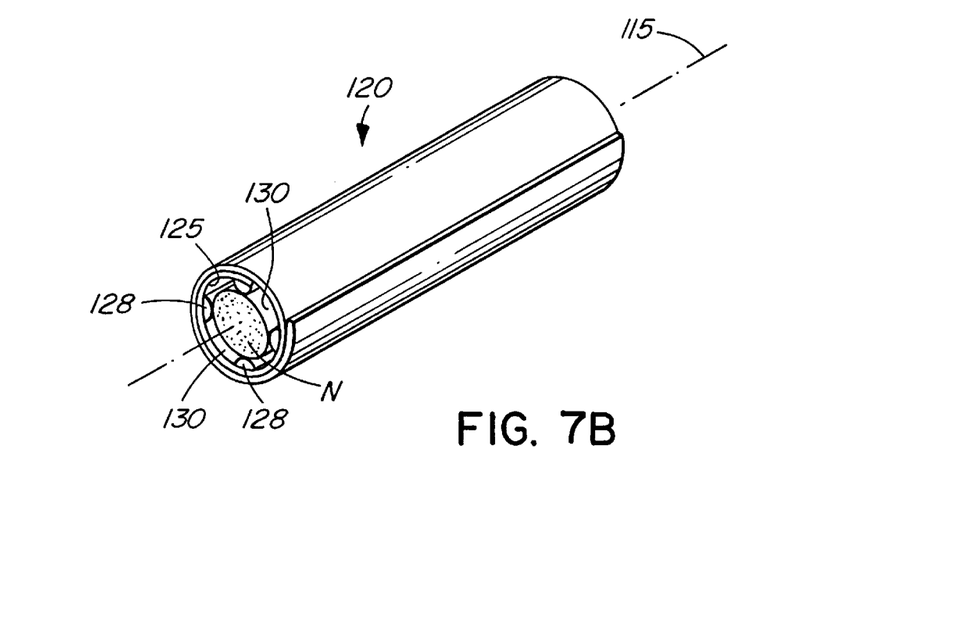

FIGS. 7A and 7B illustrate a nerve cuff 120 according to a further alternative embodiment of the invention. Nerve cuff 120 comprises a self-curling sheet 124 biased to curl upon itself around an axis 115 to form an annular nerve cuff having a bore 125. A nerve can be inserted through bore 125 by unrolling sheet 124 and then permitting sheet 124 to curl around a nerve in a controlled manner. Nerve cuffs of this general type are described in Naples et al., U.S. Pat. No. 4,602,604. A plurality of rounded ridges 128 extend along sheet 124 in a generally longitudinal direction.

When nerve cuff 120 is in its curled up configuration, as shown in FIG. 7B, ridges 128 project into bore 125 and function in the same manner as ridges 28 and 28A, which are described above, to define chambers 130 between cuff 120 and a nerve N passing through bore 125. Electrodes 134 suitable for nerve stimulation and/or recording may be provided on sheet 124 between ridges 128. In the alternative, fluid conduction means, such as tubes, may be provided to conduct fluids into or out of chambers 130.

Figure 8A:
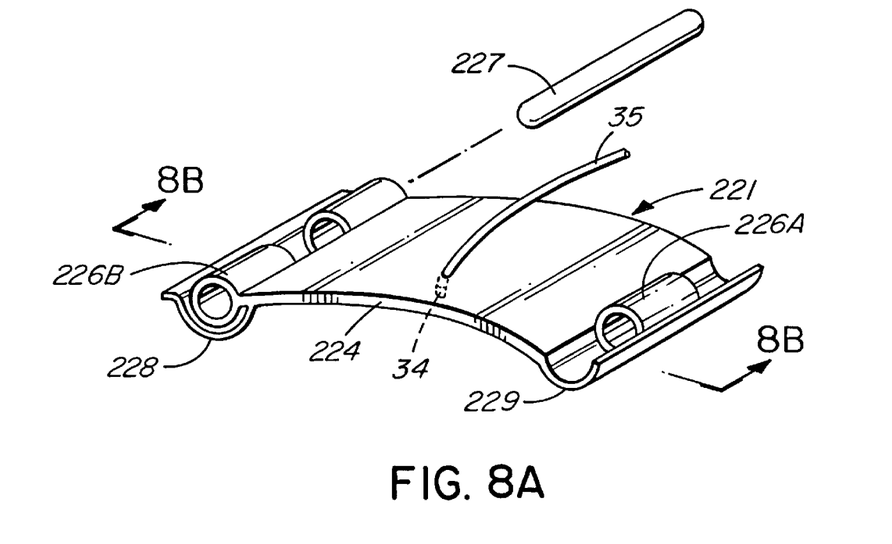
FIG. 8A is a perspective view of one segment from a multi-segmented nerve cuff according to a further alternative embodiment of the invention.
Figure 8B:
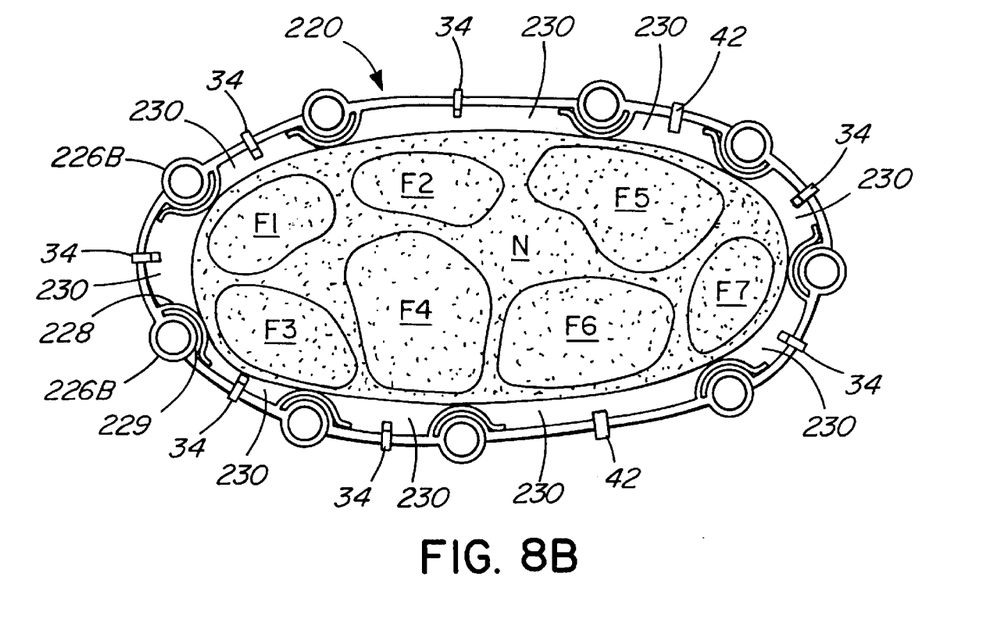
FIG. 8B is a sectional view showing a multi-segmented nerve cuff comprising a plurality of connected segments encircling a nerve; and, FIG. 8C is a sectional view of a single channel nerve cuff comprising a segment as shown in FIG. 8A retained by a flexible band.

FIGS. 8A and 8B illustrate a modular nerve cuff 220 according to the invention. Nerve cuff 220 comprises several segments 221. Each segment 221 comprises elements of a closure 226 which allows each segment 221 to be attached to adjacent segments 221. Each segment 221 comprises a flexible body wall portion 224 and a longitudinal ridge 228. When several segments 221 are assembled to form a cuff 220, as shown in FIG. 8B, then pairs of adjacent ridges 228 define chambers 230 between themselves. Ridges 228 and chambers 230 function in substantially the same manner as ridges 28 and chambers 30 described above. Each chamber 230 may bear one or more electrodes 34 and/or one or more fluid carrying tubes 42. Transverse end sealing ridges (not shown) may optionally be provided along the end edges of segments 221.

Closures 226 are preferably of the type described above. Each cuff segment 221 bears along its longitudinal edges sets of closing elements 226A and 226B. Elements 226A and 226B may be interdigitated and secured with a suitable locking member 227. Preferably, as shown in FIG. 8A, each segment 221 has a curved longitudinal flap 229 extending along a first lateral edge inwardly adjacent to members 226A. Flap 229 is preferably bonded to members 226A and seals its closure 226. In each segment 221, ridge 228 preferably comprises a curved flap extending along a second lateral edge of segment 221. Flaps 228 and 229 may be fabricated, for example, from longitudinally bisected lengths of silicone tubing or may be formed integrally with bodies 224 of cuff segments 221 by any suitable process.

As shown in FIG. 8B, when a closure 226 is closed then flaps 228 and 229 overlap along their lengths. The flap which defines ridge 228 is preferably spaced apart from flap 229 so that it can move to better conform to the outer surface of a nerve N. Longitudinal ridges 228 press against the outer epineurial sheath of a cuffed nerve N, as described above, to provide a fluid seal against nerve N.

Nerves are typically not circular in cross-section. The modular embodiment of FIGS. 8A and 8B is particularly well adapted for cuffing nerves having non-circular cross-sections. The widths of the modular cuff segments 221 may vary. In some applications it may be desirable to have some narrow segments 221 defining narrow chambers 230 and some wider segments 221 defining wider chambers 230 to better match the local anatomy of the nerve.

The modular embodiment of FIGS. 8A and 8B offers the advantages that a cuff having a desired combination of electrodes and/or tubes can be made from segments 221 equipped with different combinations of electrodes 34 and/or tubes 42. The sizing of cuff 220 can be adjusted by replacing any one or more of segments 221 with a segment 221 having a different width. It is advantageous that a cuff 220 can be readily custom fitted by a surgeon who is implanting cuff 220. During implantation, while nerve N is exposed, the surgeon can select segments 221 from a set of segments 221 of graduated widths to provide a cuff 220 which is well fitted to nerve N.

Figure 8C:
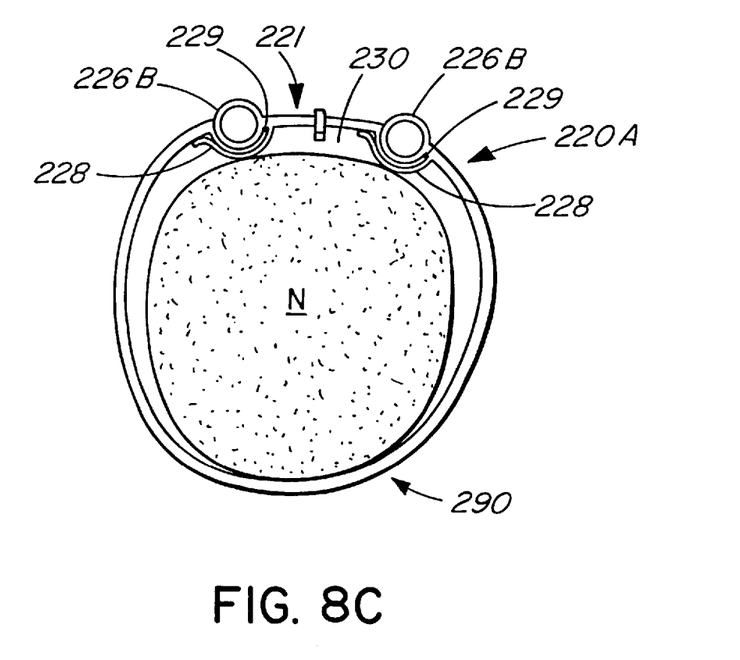

FIG. 8C is a transverse sectional view of a nerve cuff 220A comprising a single segment 221 held in place on a nerve N by means of a flexible band 290 that encircles nerve N and attaches to either side of segment 221. Band 290 may take the form of a wide segment 221. Band 290 may be perforated or apertured. This embodiment provides a single chamber 30 covering a limited region of the surface of nerve N between two ridges 228. One or more electrodes 34 and/or one or more fluid carrying tubes may communicate with the interior of chamber 30.

Those skilled in the art will appreciate that nerve cuffs according to this invention can provide better selectivity for activity in selected portions of a nerve than conventional nerve cuffs because of ridges 28, which divide the volume inside the nerve cuff and exterior to a nerve passing through the nerve cuff into a number of chambers 30 which are insulated from each other. This result is achieved without the need to penetrate the outer epineurial sheath of the nerve and without the risk of harm that such penetration could cause. A nerve cuff according to the invention may be used in anatomical areas where penetration type nerve cuffs could not be used because the outer epineurial sheath is too tough to allow penetration or because penetration would excessively damage the nerve.

As will be apparent to those skilled in the art in the light of the foregoing disclosure, many alterations and modifications are possible in the practice of this invention without departing from the spirit or scope thereof. For example, if a nerve cuff is sufficiently long then circumferential sealing ridges 33 may not be required in some applications. The dimensions and shape of the profile of ridges 28 and 33 may be varied from the shapes shown in the drawings as long as these ridges can seal against a nerve well enough to divide the space within the cuff and around the nerve into two or more isolated chambers and yet remain sufficiently soft and blunt that they do not damage the nerve passing through bore 25 by penetration or excessive indention. Chambers 30 need not extend along the entire length of cuff 20. The configurations of electrodes and/or fluid carrying tubes in chambers 30 may be varied. Accordingly, the scope of the invention is to be construed in accordance with the substance defined by the following claims.

What is claimed is:

1. A nerve cuff comprising:
   (a) an electrically insulating tubular cuff body of a biocompatible material penetrated by a bore for receiving a nerve, the cuff body having a closure for permitting passage of a nerve into the bore;
   (b) a plurality of electrically insulating blunt longitudinal ridges extending generally longitudinally on an inner surface of the cuff body and projecting into the bore, adjacent pairs of the longitudinal ridges defining a plurality of chambers extending generally longitudinally in the bore; and,
   (c) an electrode in each of a plurality of the chambers, the electrode located between a pair of adjacent ones of the longitudinal ridges.

2. The nerve cuff of claim 1 wherein each of the longitudinal ridges comprises a soft pliable material.

3. The nerve cuff of claim 2 wherein each of the longitudinal ridges comprises an elongated tubular member.

4. The nerve cuff of claim 3 wherein the longitudinal ridges extend along substantially an entire length of the cuff body.

5. The nerve cuff of claim 4 wherein the tubular member has a wall having a thickness in the range of 0.05 mm to 0.25 mm.

6. The nerve cuff of claim 1 wherein the longitudinal ridges extend substantially an entire length of the cuff body.

7. The nerve cuff of claim 6 comprising first and second circumferential sealing ridges at first and second ends of the bore wherein the longitudinal ridges extend between the first and second circumferential sealing ridges.

8. The nerve cuff of claim 7 wherein each of the longitudinal ridges has a generally semi-circular cross sectional profile.

9. The nerve cuff of claim 6 wherein the longitudinal ridges project into the bore by approximately 5% to 20% of an internal diameter of the bore.

10. The nerve cuff of claim 9 comprising a set of three spaced apart electrodes arranged in a line along each chamber midway between each pair of adjacent ones of the longitudinal ridges.

11. The nerve cuff of claim 10 wherein two outermost ones of the electrodes in each chamber are electrically shorted together.

12. The nerve cuff of claim 10 wherein the closure comprises a pair of spaced apart first apertured members affixed to the cuff body at a first edge of a slit in the cuff body, the first apertured members having apertures aligned generally with the slit; a second apertured member capable of being interdigitated between the first apertured members and affixed to the cuff body at a second edge of the slit, the second apertured member having an aperture aligned generally with said slit; and an elongated locking member capable of being inserted to extend through the apertures of the first apertured members and the second apertured member when the second apertured member is interdigitated with the first apertured members.

13. The nerve cuff of claim 1 wherein the cuff body comprises a self curling sheet biased to curl about an axis and the longitudinal ridges extend generally parallel to the axis.

14. The nerve cuff of claim 1 wherein the cuff body comprises a plurality of linked segments, each of the segments comprising a cuff body portion bearing a longitudinally extending blunt ridge member, each segment spanning a portion of a circumference of the nerve cuff.

15. The nerve cuff of claim 14 wherein the ridge member on each segment comprises a curved flap extending from the cuff body portion.

16. The nerve cuff of claim 15 wherein the curved flap on each segment extends along a lateral edge of the segment and overlaps a closure linking the segment to an adjacent segment.

17. The nerve cuff of claim 16 wherein the curved flap is spaced slightly inwardly from the closure.

18. The nerve cuff of claim 17 wherein the closure comprises two or more spaced apart first apertured members affixed to the first lateral edge of a first adjacent segment, the first apertured members having apertures aligned generally with the first lateral edge of the first segment; one or more second apertured members capable of being interdigitated between the first apertured members and affixed to a second lateral edge of a second adjacent segment, the second apertured members having apertures aligned generally with the second lateral edge of the second adjacent segment; and an elongated locking member capable of being inserted to extend through the apertures of the first apertured members and the second apertured members when the second apertured members are interdigitated with the first apertured members.

19. A nerve cuff comprising:
(a) fluid impermeable tubular cuff body penetrated by a bore for receiving a nerve, the cuff body having a closure for permitting passage of a nerve into the bore;
(b) a plurality of fluid impermeable rounded longitudinal ridges extending generally longitudinally on an inner surface of the cuff body and projecting into the bore, adjacent pairs of the longitudinal ridges defining a plurality of chambers extending generally longitudinally in the bore; and,
(c) a plurality of tubes, each one of the plurality of tubes extending into a different one of a plurality of the chambers for carrying fluid into or out of the chamber.

20. The nerve cuff of claim 19 comprising two or more tubes extending into each of one or more of the chambers.

21. The nerve cuff of claim 19 wherein each of the longitudinal ridges comprises an elongated tubular member.

22. The nerve cuff of claim 21 wherein the longitudinal ridges extend substantially an entire length of the cuff body.

23. The nerve cuff of claim 21 wherein the tubular member has a wall having a thickness in the range of 0.05 mm to 0.25 mm.

24. The nerve cuff of claim 19 comprising first and second circumferential sealing ridges at first and second ends of the bore wherein the longitudinal ridges extend between the first and second circumferential sealing ridges.

25. The nerve cuff of claim 24 wherein each of the longitudinal ridges has a generally semi-circular cross sectional profile.

26. The nerve cuff of claim 24 wherein each of the longitudinal ridges has a generally circular cross sectional profile.

27. A nerve cuff comprising:
(a) a segment comprising a cuff body wall portion;
(b) first and second longitudinally extending blunt ridge members extending along the cuff body wall portion and defining an open-sided chamber extending between the first and second ridges;
(c) a band member connectible between first and second sides of the cuff body wall portion to define a bore; and,
(d) one or more electrodes or one or more fluid conduits extending into the chamber;
wherein the band member is capable of holding the cuff body wall portion to a nerve passing through the bore with the ridges sealing against an outer surface of the nerve and the nerve closing the open side of the chamber.

28. A method for selectively interfacing to a nerve, the method comprising the steps of:
(a) providing a nerve cuff, the nerve cuff comprising:
(i) a tubular cuff body penetrated by a bore for receiving a nerve, the cuff body having a closure for permitting passage of a nerve into the bore;
(ii) a plurality of longitudinal ridges extending generally longitudinally on an inner surface of the cuff body and projecting into the bore, adjacent pairs of the longitudinal ridges defining a plurality of chambers extending generally longitudinally in the bore; and,
(iii) in at least one of the chambers, an interface comprising at least one electrode or at least one fluid port;
(b) dissecting a nerve from surrounding tissues;
(c) opening the closure and placing the cuff around the nerve with the chambers extending along portions of the nerve;

(d) closing the closure, thereby bringing the ridges into sealing contact with an outer surface of the nerve without penetrating the outer surface of the nerve; and, (e) either stimulating selected portions of the nerve by introducing electrical signals via the at least one electrode or pharmacological agents via the at least one fluid port into selected ones of the chambers or monitoring selected portions of the nerve by measuring electrical potentials in the chambers or sampling fluids from the chambers.

* * * * *